(12) United States Patent
Korman

(10) Patent No.: US 9,814,528 B2
(45) Date of Patent: Nov. 14, 2017

(54) METHOD AND SYSTEM FOR IN SITU TISSUE EXPANSION

(71) Applicant: Marz Medical, Inc., Mountain View, CA (US)

(72) Inventor: Joshua Korman, Los Altos Hills, CA (US)

(73) Assignee: Marz Medical, Inc., Mountain View, CA (US)

( * ) Notice: Subject to any disclaimer, the term of this patent is extended or adjusted under 35 U.S.C. 154(b) by 0 days.

(21) Appl. No.: 14/997,235

(22) Filed: Jan. 15, 2016

(65) Prior Publication Data

US 2016/0128794 A1 May 12, 2016

Related U.S. Application Data

(62) Division of application No. 13/592,138, filed on Aug. 22, 2012, now Pat. No. 9,265,921.

(60) Provisional application No. 61/526,123, filed on Aug. 22, 2011.

(51) Int. Cl.
*A61M 29/02* (2006.01)
*A61B 19/00* (2006.01)
*A61B 90/00* (2016.01)
*A61M 25/10* (2013.01)

(52) U.S. Cl.
CPC .............. *A61B 19/24* (2013.01); *A61B 90/02* (2016.02); *A61M 25/10181* (2013.11); *A61M 25/10187* (2013.11); *A61M 29/02* (2013.01); *A61M 25/1018* (2013.01)

(58) Field of Classification Search
CPC .... A61M 29/02; A61M 25/1018; A61B 19/24

USPC ................ 606/190, 191, 192, 194, 195, 198
See application file for complete search history.

(56) References Cited

U.S. PATENT DOCUMENTS

| | | |
|---|---|---|
| 4,955,905 A | 9/1990 | Reed |
| 5,005,591 A | 4/1991 | Austad |
| 5,092,348 A | 3/1992 | Dubrul et al. |
| 5,496,368 A | 3/1996 | Wiese |
| 5,549,672 A | 8/1996 | Maddock et al. |
| 6,432,081 B1 | 8/2002 | Atala |
| 6,668,836 B1 | 12/2003 | Greenburg et al. |
| 9,265,921 B2 | 2/2016 | Korman |
| 2004/0147953 A1 | 7/2004 | Gedebou |
| 2008/0051822 A1 | 2/2008 | Widgerow |
| 2010/0010531 A1 | 1/2010 | Shalon et al. |
| 2011/0152913 A1 | 6/2011 | Jones et al. |

(Continued)

OTHER PUBLICATIONS

Logan, et al. A control unit for maximal-rate continuous tissue expansion (CTE). Biomed Sci Instrum. 1989;25:27-33.

(Continued)

*Primary Examiner* — Vy Bui
(74) *Attorney, Agent, or Firm* — Wilson Sonsini Goodrich & Rosati

(57) ABSTRACT

Tissue expansion system includes a pump, a controller, and inflatable bladder, and a pressure sensor. The pump is adapted for substantially continuous operation in response to a pressure within a subcutaneously implanted inflatable bladder. The pump is thus able to deliver inflation medium to the bladder when the pressure within the bladder is below a predetermined lower threshold while stopping delivery of the fluid when the pressure rises above a higher threshold or reaches a predetermined maximum volume.

11 Claims, 2 Drawing Sheets

(56) References Cited

U.S. PATENT DOCUMENTS

2013/0079807 A1    3/2013  Korman

OTHER PUBLICATIONS

Office action dated Apr. 9, 2015 for U.S. Appl. No. 13/592,138.
Office action dated Sep. 11, 2015 for U.S. Appl. No. 13/592,138.
Notice of allowance dated Dec. 8, 2015 for U.S. Appl. No. 13/592,138.

METHOD AND SYSTEM FOR IN SITU TISSUE EXPANSION

CROSS-REFERENCE TO RELATED APPLICATIONS

This application is a divisional of U.S. patent application Ser. No. 13/592,138, filed on Aug. 22, 2012, which claims the benefit of provisional application No. 61/526,123, filed on Aug. 22, 2011, the full disclosures of which are incorporated herein by reference.

BACKGROUND OF THE INVENTION

1. Field of the Invention

The present invention relates generally to medical methods and devices. More particularly, the present invention relates to methods for expanding tissue using systems which monitor inflation pressure of an implanted expandable bladder.

Tissue defects in the skin and other tissues occur from a variety of causes including surgery, burns, traumatic injury, and congenital deformities. Such defects are often characterize by tissue "deficits" where there is insufficient skin or tissue present to cover or fill the affected body region in a normal or desired profile or pattern.

Tissue deficit may be treated by stimulating skin and/or tissue growth in the region of the defect. For example, "tissue expanders" may be implanted beneath a region of skin or within a volume of tissue which suffer from the deficit. By gradually inflating or otherwise expanding such tissue expander, the growth of skin and/or tissue can be promoted.

Presently, most tissue expanders are in the form of an implantable balloon with a valve that allows a physician to periodically inflate the balloon to increase its volume over successive office visits. As the patient will or typically visit the doctor only about once per week, such periodic inflations often require relatively large volumes of inflation medium which can cause not only patient discomfort, but also tissue ischemia, concavities to underlying structures such as bone, and induce encapsulation of the implant causing capsular contraction and stiffening tissue around the expander.

In order to address such shortcomings, a number of "continuously" expanding devices have been proposed. For example, in U.S. Patent Publication 2010/0010531, a device is described which allows the patient to periodically trigger a gas source within the implanted expander. Allowing the patient to control expansion, however, has its own drawbacks, and the patient will seldom follow an optimum inflation protocol to achieve the desired tissue expansion. Moreover, the use of a gas as the inflation medium is also disadvantageous.

For these reasons, it would be desirable to provide improved and alternative tissue expansion devices. In particular, it would be desirable to provide such devices which continuously and automatically deliver an inflation medium to an implanted expander over time in a more optimal and controlled pattern. It would be further desirable if such expanders and their supporting systems were adapted for patient convenience and comfort to further promote their use. At least some of these objectives will be met by the inventions described here and below.

2. Description of the Background Art

Relevant patents and publications include U.S. Pat. Nos. 6,668,836; 6,432,081; 5,549,672; 5,496,368; 5,005,591; 5,092,348; 4,955,905; and U.S. Patent Publications 2011/152913; 2010/010531; 2008/051822; and 2004/147953. See also Logan and Hayden (1989) ISA, Paper #89-0207, pp. 27-33.

SUMMARY OF THE INVENTION

The present invention provides methods and systems which provide continuous, automated tissue expansion of a patient's skin or other tissue. By "continuous" it is meant that the device will periodically deliver an inflation medium to an implanted expandable bladder in response to a monitored value, typically pressure within the inflatable bladder. By "automated" it is meant that the inflation of the tissue bladder or other expander will be initiated by the system itself, not by intervention from a physician or other personnel. Usually, as described below, the systems of the present invention will include an automated controller for monitoring the pressure or other patient value and for controlling a pump or other inflation medium delivery mechanism. Typically, the systems will maintain the pressure in the device at a level below 35 mmHg (in a range from 5 mmHg to 35 mmHg), usually below 20 mmHg, and most often at a level which does not exceed 5-10 mmHg.

The tissue expansion component of the systems of the present invention will typically be an expandable bladder of the type which can be inflated with an inflation medium. The inflation medium is usually an "incompressible" medium, typically being a liquid, usually being saline or other biocompatible liquid medium. The bladder will have an expandable wall, usually being formed from an elastic material, such as silicone rubber or elastomer or the like. In other cases, the bladder could be at least partially formed from an inelastic or non-distensible material, such as a variety of inelastic polymers. In all cases, however, the expandable bladder will be configured to allow for controlled expansion. In the case of inelastic materials, the bladders will typically be pleated, folded, rolled or otherwise configured to allow unfurling during deployment. In general, the present invention can be used with any known or yet to be developed expandable device of the type intended to be implanted for tissue expansion.

The present invention specifically provides for monitoring of the pressure within the inflatable bladder or other tissue expander. Usually, the pressure will be monitored by a pressure sensor in an external portion of an inflation medium supply, i.e. one of the components which is not implanted. In other cases, however, it would be possible to deploy a pressure sensor within the inflatable bladder itself and/or a portion of an inflation medium feed tube connected to the bladder. Suitable pressure sensors include conventional piezoelectric transducers of the type which are conventionally used for pressure monitoring. The pressure will typically be monitored continuously in real time, but in another instance the pressure need only be monitored periodically at intervals separated by discrete time periods. Usually, however, the pressure will be monitored at least once each hour, typically being monitored much more often if not continuously.

The incompressible or other inflation fluid will be introduced into the expandable bladder whenever the monitored pressure falls below a lower threshold level, typically in the range from 0 mm Hg to 30 mm Hg. The lower threshold level will typically be held constant throughout an individual treatment, but could sometimes be changed at different times during the treatment protocol.

The introduction of incompressible inflation fluid will be terminated after a predetermined endpoint has been reached.

The endpoint will typically occur when a higher pressure threshold has been reached within the expandable bladder typically in the range from 40 mm Hg to 50 mm Hg. The upper range, however, can be reduced when the integrity of the skin is compromised, for example when the skin has been previously compromised. Usually, the difference between the upper and lower pressure thresholds is at least 10 mm Hg, sometimes being as much as 20 mm Hg or more. In this way, expandable bladder can be inflated to a maximum pressure selected to effectively expand or distend the skin and tissue while causing minimum discomfort and reducing any side effects from such expansion. Only after the pressure returns to near a base level is additional fluid introduced to again raise the pressure to a level at or near a determined maximum value.

While relying on upper and lower pressure thresholds will usually be the preferred method for tissue expansion, in alternative embodiments a predetermined volume of fluid may be introduced whenever the pressure falls to or below the lower value described above. Such a predetermined volume of fluid will typically be in the range from 0.5 cc to 10 cc, usually from 3 cc to 5 cc, where the volume will be selected to provide effective tissue expansion with minimum risk of patient discomfort and trauma to the tissue. Still further alternatively, it would be possible to deliver a continuous flow or liquid fluid at a relatively low rate, e.g., 0.5 ml/hr to 3 ml/hr, for periods of hours or days, depending on the flow rates.

The methods of the present invention may find use whenever it is desirable to expand skin or other tissue surface, for example following breast reconstructive surgery (mastectomies), when expanding tissue to be used for covering burn tissue or other defects, and the like. In a particular embodiment, the expandable bladder may be implanted in a subpectoral pocket following a mastectomy with or without an accelular dermal matrix. In such cases, the expandable bladder may be initially inflated with a small volume of saline or other inflation medium, typically in the range from 50 cc to 100 cc. In alternative embodiments, the expandable bladder may be implanted beneath skin or other tissue adjacent to a tissue defect. In such cases, the bladder will be inflated to expand the skin or tissue, and the expanded tissue will create a "flap" that can be used to cover the defect. When used following mastectomies, the bladder may optionally be left in place to provide the "breast implant". Typically, the inflation tube as described below will be removed and the inflation chord in the bladder permanently sealed. In other procedures, the implant will typically be removed.

The present invention provides systems for expanding tissue and performing the methods as described above. The systems of the present invention comprise an expandable bladder adapted to be located beneath the region of the skin or other tissue to be expanded. The systems further comprise a pump adapted to be connected to a source of inflation medium, typically saline or other non-compressible medium, in order to deliver the inflation medium to the expandable bladder. A pressure sensor adapted to monitor pressure within the expandable bladder (either directly or indirectly) on a substantially continuous basis is connected to a controller which receives such pressure data. The controller controls the pump to deliver inflation medium to the bladder whenever the pressure falls below a lower threshold value.

The systems of the present invention may further comprise a portable carrier which holds at least the pump, pressure sensor, and controller. The portable carrier may be in a form adapted to be worn by a patient, such as a vest, backpack, belt or the like. Alternatively, the carrier may be adapted with a handle or other means for allowing the patient to carry the carrier along with her or him.

The controller will typically be programmed to deliver the inflation medium until a monitored pressure in the implant pressure reaches an upper threshold value, where the lower and upper threshold values are within the ranges set forth above. Alternatively, the controller may be programmed to deliver preselected inflation volumes after the lower threshold value has been reached and regardless of the higher pressure which is eventually achieved. The controller will typically be further programmed to stop delivering inflation medium entirely after a target total volume of the inflation medium has been delivered to the patient. In the case of post-mastectomy treatment, the total inflation medium delivered to the inflatable bladder will typically be in the range from 150 cc to 800 cc, more typically from 200 cc to 600 cc.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
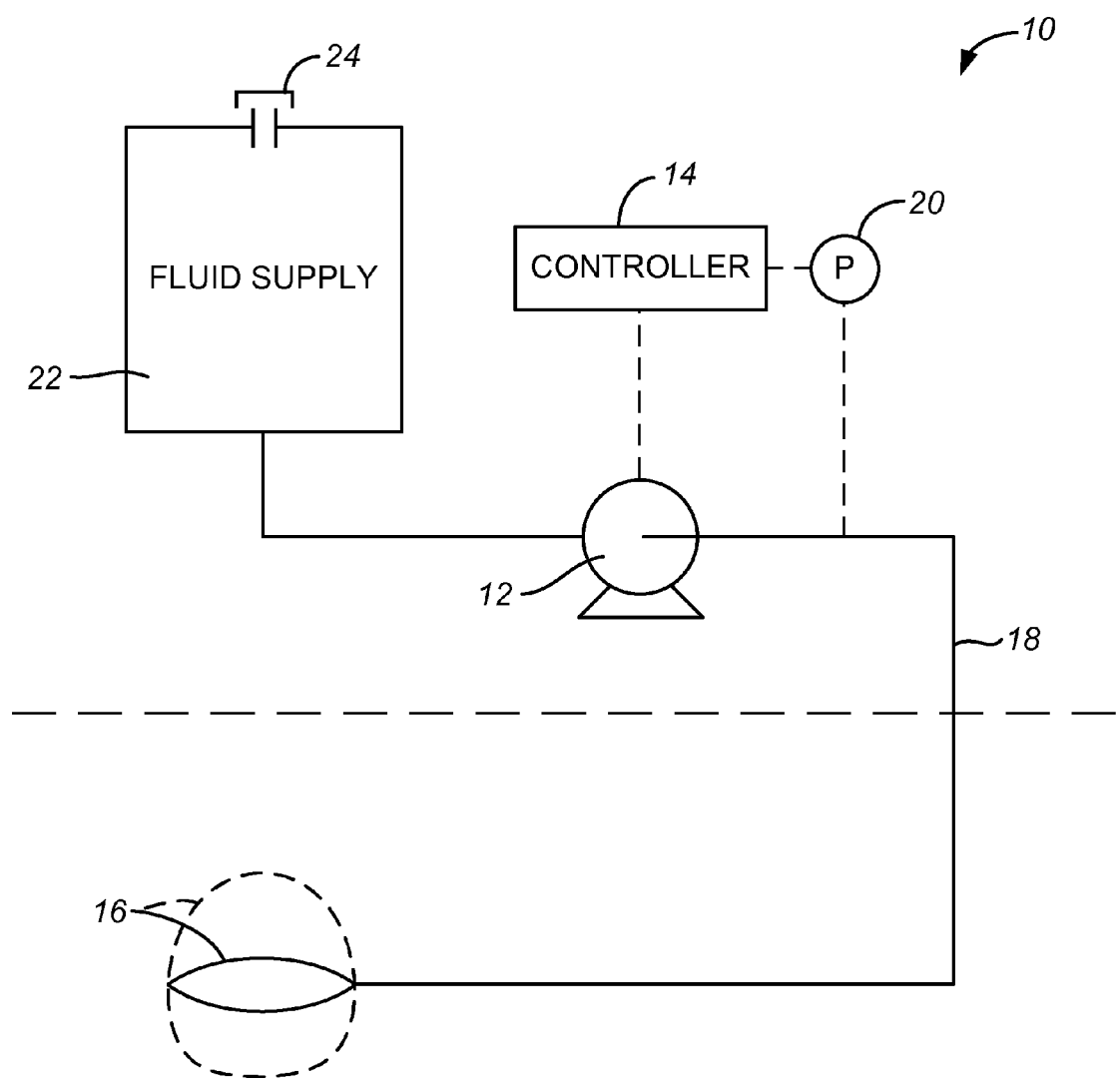
FIG. 1 is a block diagram illustrating the system components of the systems of the present invention.

Referring to FIG. 1, a system 10 constructed in accordance with the principles of the present invention comprises a pump 12, a controller 14, and an inflatable bladder 16 connected to the pump by connecting tube 18. A pressure sensor 20 is connected to the connecting tube 18 (directly or indirectly) so that it may sense a static pressure within the inflation bladder 16. The pressure sensor is also connected to the controller 14 to provide a continuous realtime or periodic reading of the pressure in the bladder to the controller. The controller 14 typically comprises a digital microprocessor which has been programmed by conventional means to control the pump 12 as described above. A fluid supply 22, typically comprising an incompressible liquid such as saline, is attached to an input port of pump 12 so that it may be, in turn, be pumped to the inflatable bladder 16. The fluid supply typically has a port 24 to allow refilling of the supply with the desired fluid. Most portions of these system 10 will be maintained externally to the patient, as shown above the broken line in FIG. 1, while the inflatable bladder 16 and a portion of the connecting tube 18 will be implanted in the patient (below broken line). Typically, the connecting tube 18 will be transcutaneously placed through the patient's skin and have a connecting end adapted for removable connection to the pump. Alternatively, the inflatable bladder may be connected through a connection port which lies substantially at the patient's skin just beyond the transcutaneous insertion point. The corresponding portion of the tube may then be connected and disconnected from the pump as desired.

Figure 2:
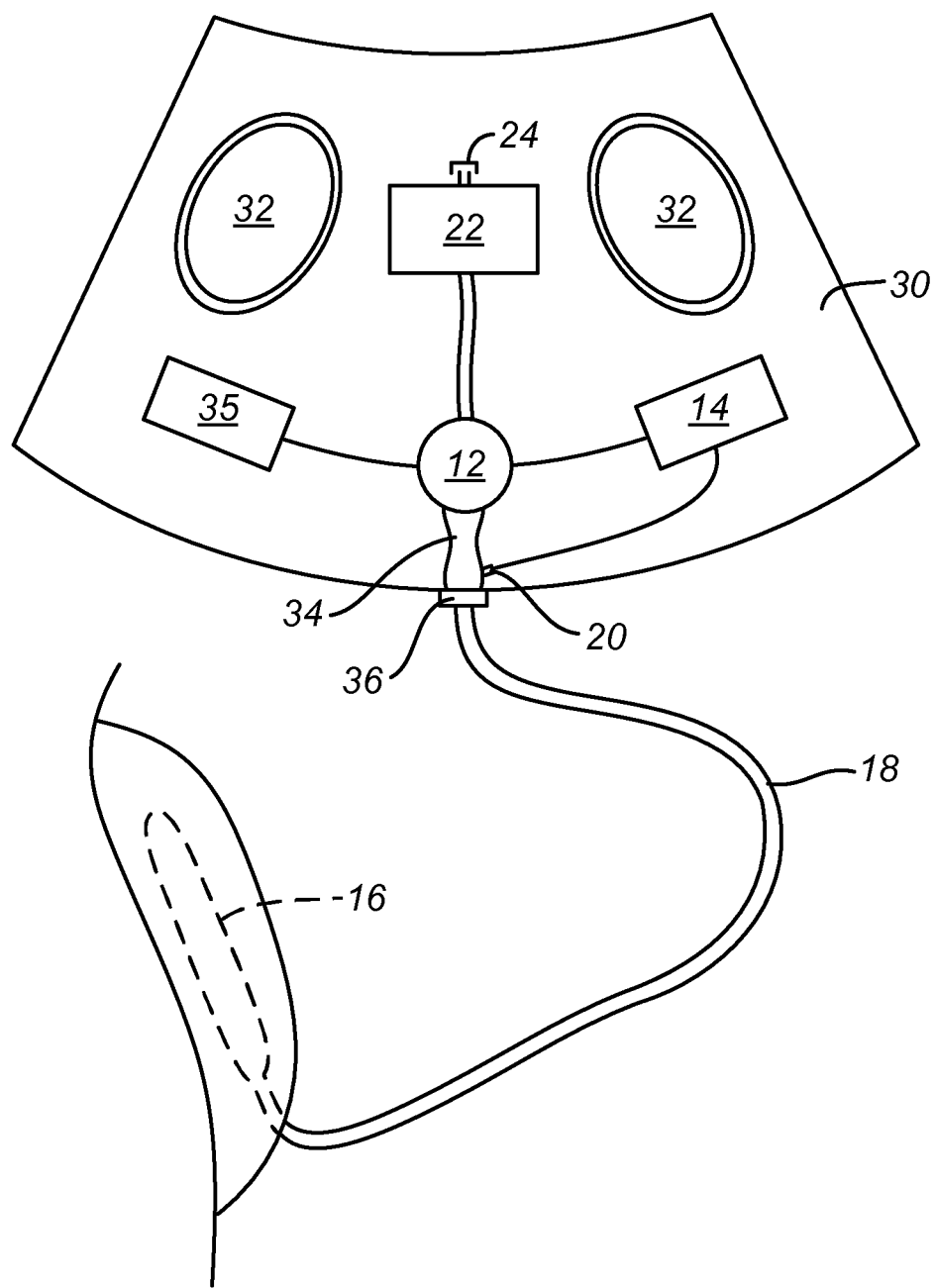
FIG. 2 illustrates a vest adapted to carry certain system components used with an implantable inflatable bladder according to the present invention.

As illustrated in FIG. 2, the external system components of the system 10 may be mounted on a patient-wearable support, such as vest 30. The vest 30 may have the general layout of a vest garment including armholes 32, and will be further provided with the system components mounted on an interior and/or exterior surface thereof. As shown in FIG. 2, the pump 12 includes a short connecting tube 34 which extends to a connecting port 36 which may be removably attached to the connecting tube 18. The pressure sensor 20 may be located on the tube 34. Typically, a battery 35 or other power supply will also be provided to power the pump and controller.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for expanding tissue, said system comprising:
an expandable bladder adapted to be located beneath a region of skin to be expanded;
a pump adapted to be connected to a source of inflation medium and to deliver a predetermined volume of said inflation medium to the expandable bladder at a flow rate of 0.5 milliliters per hour to 3 milliliters per hour for a predetermined interval;
a pressure sensor adapted to monitor pressure within the expandable bladder on a substantially continuous basis;
a controller which receives pressure data from the pressure sensor and controls the pump to deliver inflation medium to the bladder when the pressure falls below a lower threshold value; and
a portable carrier which holds the pump, pressure sensor, and controller, wherein the portable carrier is adapted to be worn by a patient,
wherein the controller is configured to control the pump to deliver the inflation medium, terminate delivery of the inflation medium, and resume delivery of the inflation medium after the predetermined interval, and
wherein the controller is programmed to stop delivering inflation medium after a target total volume of inflation medium has been delivered to the patient, the target total volume of inflation medium comprising a plurality of the predetermined volumes delivered.

2. A system as in claim 1, wherein the portable carrier comprises a vest, a backpack, or a belt.

3. A system as in claim 1, wherein the controller is programmed to deliver inflation medium until the pressure reaches an upper threshold value.

4. A system as in claim 3, wherein the upper threshold level is in the range from 5 mmHg to 35 mmHg.

5. A system as in claim 1, wherein the target total volume of inflation medium is in the range from 150 cc to 800 cc.

6. A system as in claim 5, wherein the target total volume of inflation medium is in the range from 200 cc to 600 cc.

7. A system as in claim 1, wherein the expandable bladder is configured to be placed in a subpectoral pocket of the patient following a mastectomy.

8. A system as in claim 7, wherein the expandable bladder is initially inflated with a volume of saline in the range from 50 cc to 100 cc.

9. A system as in claim 1, wherein the controller is programmable.

10. A system as in claim 1, wherein the predetermined interval is at least one hour.

11. A system as in claim 1, wherein the inflation medium comprises saline.

* * * * *